United States Patent [19]
Brosnahan

[11] Patent Number: 5,626,580
[45] Date of Patent: *May 6, 1997

[54] MULTI-SECTION INTRAMEDULLARY NAIL

[76] Inventor: Robert Brosnahan, 2936 Waterleaf, Germantown, Tenn. 38138

[*] Notice: The term of this patent shall not extend beyond the expiration date of Pat. No. 5,620,445.

[21] Appl. No.: 275,783

[22] Filed: Jul. 15, 1994

[51] Int. Cl.$^6$ .................................................. A61B 17/56
[52] U.S. Cl. ..................... 606/63; 606/62; 606/68
[58] Field of Search ............................. 606/62, 63, 64, 606/65, 66, 67, 68; 623/23; 403/334

[56] References Cited

U.S. PATENT DOCUMENTS

| | | | |
|---|---|---|---|
| 1,542,266 | 6/1925 | Palmer et al. | 403/334 |
| 3,846,846 | 11/1974 | Fischer . | |
| 4,622,959 | 11/1986 | Marcus . | |
| 4,776,330 | 10/1988 | Chapman et al. . | |
| 4,805,607 | 2/1989 | Engelhardt et al. . | |
| 4,827,917 | 5/1989 | Brumfield . | |
| 4,858,601 | 8/1989 | Glisson . | |
| 4,875,475 | 10/1989 | Comte et al. . | |
| 4,940,467 | 7/1990 | Tronzo | 606/66 |
| 4,995,883 | 2/1991 | Demane et al. | 623/23 |
| 5,047,033 | 9/1991 | Fallin | 606/87 |
| 5,108,452 | 4/1992 | Fallin | 623/23 |
| 5,122,141 | 6/1992 | Simpson et al. | 606/62 |
| 5,352,227 | 10/1994 | O'Hara | 606/63 |

FOREIGN PATENT DOCUMENTS 1031128  6/1953  France .

*Primary Examiner*—Michael Powell Buiz
*Assistant Examiner*—Mark S. Leonardo
*Attorney, Agent, or Firm*—Pravel, Hewitt, Kimball & Krieger

[57] ABSTRACT

A modular intramedullary nail includes three connectable sections that are connectable end to end. The three sections include an upper proximal nail component, a lower distal nail component, and a central nail component. The nail components are connected and the end using corresponding frustroconical socket and frustroconical projecting end portions of adjoining end nail components that can be fitted together with a taper lock or morse taper connection and secured tightly together upon impact. Upon assembly, the connections are self orienting, providing corresponding key and slot portions adjacent the respective frustroconical socket and frustroconical projecting end portions of the nail components. The interlocking keys and slot align and abut upon assembly so that the adjoining nail components only align in one relative rotational position.

11 Claims, 2 Drawing Sheets

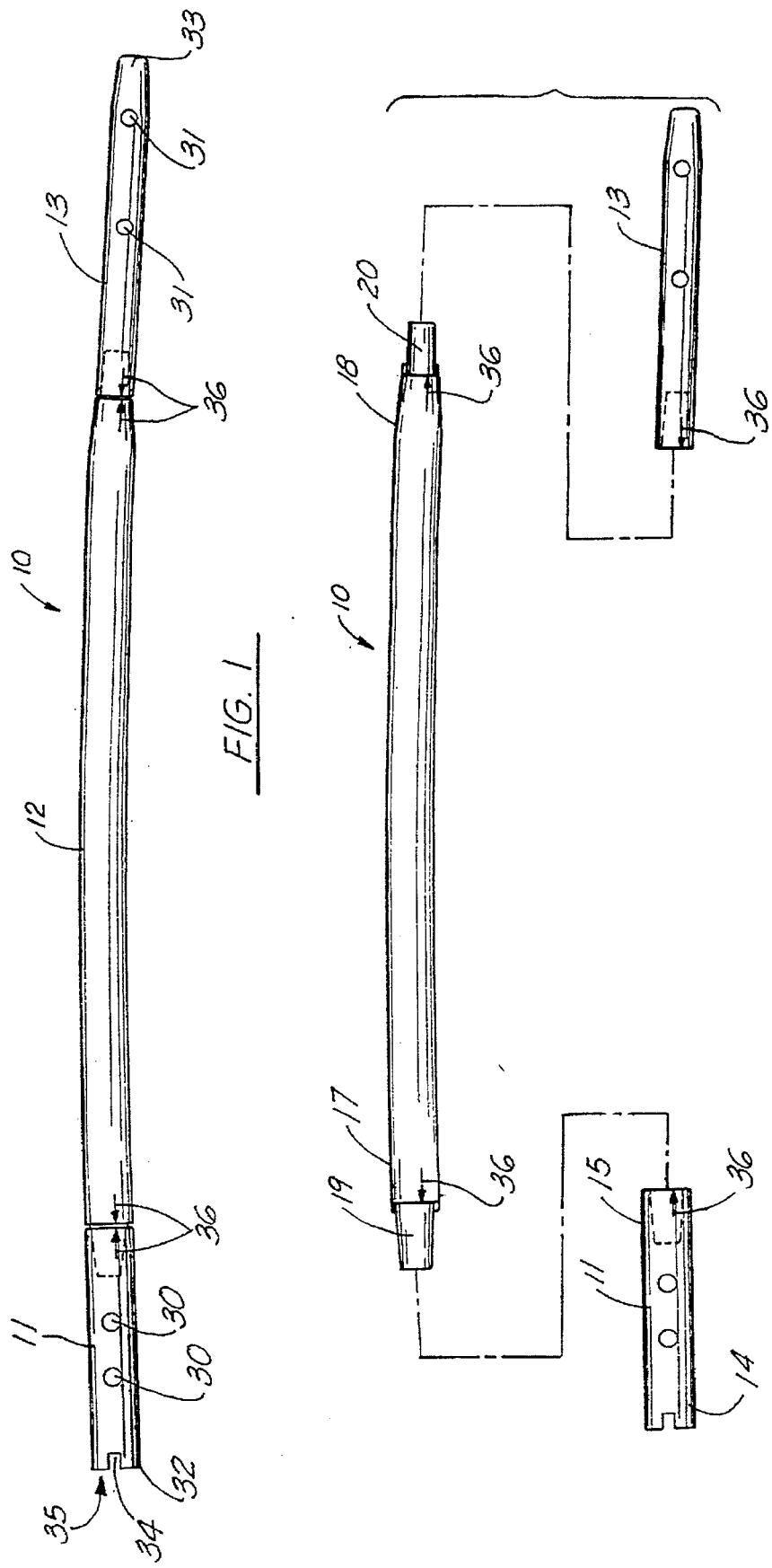

MULTI-SECTION INTRAMEDULLARY NAIL

SPECIFICATION

1. Field of the Invention

The present invention relates to an intramedullary nail system for the repair of long bone fractures, which has a multi-section modular design for enabling a surgeon to assemble a nail or related implant during surgery which most closely fits the patient's needs.

2. Background of the Invention

Intramedullary nails have become the preferred implant treatment in many long bone fracture cases. As the use of intramedullary nails has become more popular, the design of the implants has advanced so that there are particular designs for different types of fractures. Nails having a particular configuration are desirable for certain indications. Because of wide variation of the long bones in patients, the particular style of nail is preferably available in a range of lengths, diameters, and shapes. As a result, the surgeon must have at hand a large inventory of styles and sizes to accommodate the variety of indications. Examples of such styles include, but are not limited to femoral reconstruction, intramedullary hip screw, and femur components of total hips.

One solution to this variation problem is to provide a modular nail system where a surgeon can select various component parts and assemble them to fit a particular patient's needs. Such a system is taught in U.S. Pat. No. 4,805,607 to Engelhardt et al. where a modular intramedullary nail system has elongated base nails and extension members of different lengths and diameters. The base nail is the primary structural component of the system and the extension member is designed to fit on the proximal end of a base nail. By selecting various combinations of base nails and extension members, nails of a desired length and diameter can be constructed. The component parts are locked together by a pair of snap lock springs formed on the proximal end of the base nail, which include engagement tongs with locking barbs at the trailing end which are radially depressed in order to engage a counterbore on the extension member. A screw is inserted through a hole in the modular components after the rod has been implanted for preventing the tongs from disengaging.

Another intramedullary nail is disclosed in the Simpson et al. U.S. Pat. No. 5,122,141, entitled "Modular Intramedullary Nail". In the Simpson patent, an intramedullary nail system and method for providing a capability of creating intramedullary nails of any desired length includes a combination of a small number of base nail members adapted to be joined to any one of a variety of hollow extension nail members. Any selected extension nail member may be axially connected to any selected base nail member in order to prevent axially separation of the members. Additionally, each extension nail members provided with transverse openings adapted to receive a bone screw to secure the intramedullary nail within the bone to be repaired. The extension nail member is infinitely rotationally adjustable about the axis of the base nail member in order to enable the fixation of the extension member with any desired degree of anteversion prior to final assembly of the base nail member with the extension nail member.

The Comte et al. U.S. Pat. No. 4,875,475 shows a device for treating a bone that includes an intramedullary nail adapted to be driven into a hollow bone. The proximal terminal nail segment includes an internal thread and a transversely penetrating longitudinal slot adapted to receive a screw to penetrate through the nail, and to be screw connected to the bone. A distal terminal nail section comprises two transversely throughgoing bores, each adapted to receive a screw to be screw connected with the bone.

The Chapman et al. U.S. Pat. No. 4,776,330 discloses a modular femoral implant system for use in the treatment of femoral disorders resulting from injury, disease, or congenital defects. The modular system includes at least three interconnected components, including an elongated epiphyseal-metaphyseal implant, an intramedullary rod, and an angled side plate having an elongated plate portion adapted to be secured to the outer cortical wall, and a hollow sleeve adapted to extend into the femur.

A French Patent No. 1,031,128 relates to a femoral nail of multiple sections.

The Fischer U.S. Pat. No. 3,846,846 discloses a ball-shaped portion to form part of the hip joint and a second portion that extends from the ball-shaped portion into the femur. The second portion is provided with a passage through which an elongated expander rod is extended which is also to be inserted into an opening in the femur and on the expanded rod is arranged a series of expansion elements in the form of a row which as the expander rod is moved longitudinally of the row are all expanded to anchor the prosthesis to the femur.

An adjustable compression bone screw is disclosed in the Glisson U.S. Pat. No. 4,858,601 that includes a shaft having first and second sections each with an external thread that may be rotated as a unit or independently. The screw includes means adapted to receive a first driving tool for driving the shaft as unit, and further adapted to receive a second driving tool for rotating the second section independently of the first section.

The Tronzo U.S. Pat. No. 4,940,467 discloses a variable length fixation device for insertion into a hole formed in two or more bone fragments and includes a barrel portion and a fastener element. The device is used for repair of the proximal portion of a patient's femur.

The Marcus U.S. Pat. No. 4,622,959, entitled "Multi Use Femoral Intramedullary Nail", discloses an intramedullary nail for use in fractures for the left or right femur and includes a body having a head, an intermediate portion, and a distal tip. Transverse openings are provided in the body near the distal tip and in the head for receiving locking screws. One opening in the head has its axis within the femoral neck and another opening has its axis generally transverse thereto. The nail head has a seat with a transverse locating slot for securing a screw insertion tool in a fixed angular position in which the screw guide on the tool is aligned with one of the screw receiving openings.

The Brumfield U.S. Pat. No. 4,827,917, entitled "Femoral Fracture Device," provides an apparatus for treating fractures of the femur that includes a screw and an intramedullary rod. The screw has a threaded portion and a smooth portion. The rod has a head, stem, and longitudinal bore. There is at least one pair of coaxial holes through the stem, transverse to the longitudinal axis of the rod, for receiving first anchoring means such as a nail, screw, or bolt, to secure the rod within the marrow canal of the femur. There are at least a proximal pair of coaxial holes and a distal pair of coaxial holes in the head of the rod in an angled direction toward the femoral head relative to the longitudinal axis of the rod. The distal pair of head holes are adapted to slidingly receive the screw to permit the threaded portion of the screw, in use, to engage the femoral head and to allow sliding compression of a femoral neck or intertrochanteric fracture.

An optional second anchoring means which will also allow sliding and compression and an optional set screw are also provided to adapt the fracture device to a variety of applications.

U.S. Pat. No. 4,995,883, issued to DeMane et al. and U.S. Pat. No. 5,108,452, issued to Thomas W. Fallin, both entitled "Modular Hip Prosthesis," disclose a modular hip prosthesis that can be custom fitted to a particular patient by a surgeon prior to surgical insertion. The prosthesis features a body having a neck portion for carrying a rounded head element, a transitional mid-section of the prosthesis body includes generally rectangular and generally rounded cross-sectional areas, and a stem section has a generally rounded cross-sectional area. The stem is tapered to receive a tubular extension sleeve with a hollowed portion corresponding in shape to the stem portion of the prosthesis. The tubular extension sleeve has an open end portion receptive of the lower tapering stem of the prosthesis body. The stem portion including an internal bore, and an attachment in the form of an elongated screw is provided for connection to the stem internal bore for securing the extension sleeve and the prosthesis body together, forming a compressive sealed connection therebetween. Pads can be attached to the transitional midsection of the prosthesis body for increasing the cross-sectional shape of the prosthesis at the transitional midsection. Removable collars can be added to the prosthesis to form a transverse load carrying interface with the upper end of the patient's femur. Frustroconically shaped extension sleeves can be added to the prosthesis neck for extending the neck length.

U.S. Pat. No. 5,047,033, issued to Thomas W. Fallin, entitled "Mill And Guide Apparatus For Preparation Of A Hip Prosthesis," discloses a guide apparatus for preparing the femur of a patient with a rotary mill to receive a femoral hip prosthesis includes a V-shaped guide body having a lower end base portion adapted to extend into the intramedullary canal of the femur and an upper end portion comprised of at least two spaced apart struts so that the overall guide body had a configuration substantially the same as the prosthesis body sought to be implanted in the patient. The lower end of the guide body base provides one or more hemispherical receptacles for holding the hemispherical end portion of a spinning mill bit. A preferably removable transverse guide rail has connection pins at one end portion thereof for forming a connection with the upper end of the guide body at one of the struts, the arm having a curved surface that is adapted to guide the mill bit during preparation of the intramedullary canal of the patient's femur for receiving a hip prosthesis thereafter.

SUMMARY OF THE INVENTION

The present invention is directed to improved intramedullary nails providing a modular intramedullary nail system having three modular components. The components include proximal, central, and distal nail sections. The modular components of the present invention are quickly and easily assembled having joints of high mechanical and torsional integrity.

The modular components of the present invention preferably include a locking mechanism for connecting and locking together adjacent modular components which can quickly provide a positive locking fit that resists relative twisting or rotational movement between the components as well as translation.

Assembly of the modular components of the present invention is achieved by one modular component having a socket with a conical tapered surface adapted to securely engage a cooperating tapered pin or projecting conical surface. The engagement results in a secure taper lock or wedge lock connection which is resistant to translational forces. An example of a modified taper and bore providing such secure connection is a configuration known as a morse taper.

Resistance to rotational movement between adjacent nail section is achieved by providing a pair of keys adjacent each taper that engage corresponding key slots of the adjoining nail component.

In a preferred embodiment, the keys and slots are prepositioned to provide an alignment mechanism to ensure the components are properly assembled in a pre-selected position of anteversion.

In an alternative embodiment, the taper or bore of one component may be adapted to accept more than one type of mated component, with each match corresponding to direct assembly of a specific implant design.

BRIEF DESCRIPTION OF THE DRAWINGS

In order to acquire a better understanding of the invention, reference may be had to a detailed description of exemplary embodiments set forth below, to be considered along with the appended drawings, in which:

FIG. 1 is a side, partially exploded view of the preferred embodiment of the apparatus of the present invention;

FIG. 2 is an exploded side view of the preferred embodiment of the apparatus of the present invention;

DESCRIPTION OF THE EXEMPLARY EMBODIMENTS

Figure 3:
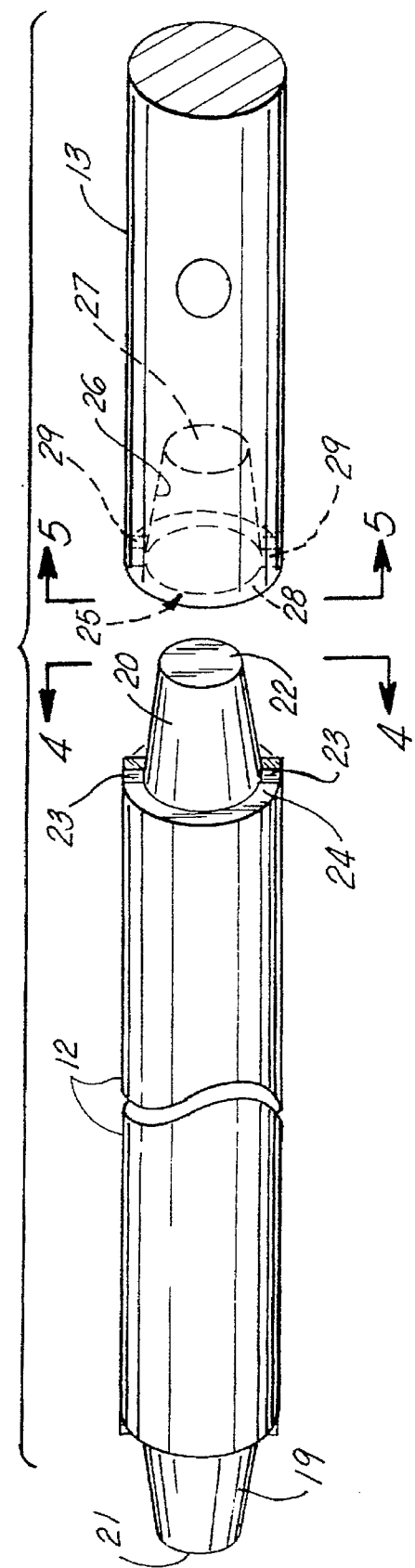
FIG. 3 is an exploded fragmentary side view of the preferred embodiment of the apparatus of the present invention.

FIGS. 1–5 illustrate the preferred embodiment of the apparatus of the present invention illustrated generally by the numeral 10. Modular intramedullary nail 10 includes three sections that are connectable end-to-end. The three sections include proximal nail section 11, central nail section 12, and distal nail section 13. As shown in FIG. 1, the modular intramedullary nail 10 is slightly curved.

Proximal nail section 11 includes opposing end portions 14, 15. The end portion 14 defines the upper portion of the assembled modular intramedullary nail 10. The numeral 32 designates the proximal end of the entire nail 10 upon assembly. End portion 15 provides a socket 16 that is frustroconically shaped. Socket 16 of nail section 11 connects to central nail section 12 at frustroconical projection 19.

Figure 5:
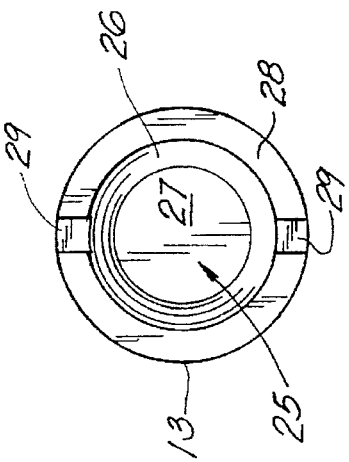
FIG. 5 is another fragmentary end view of the preferred embodiment of the apparatus of the present invention.
Figure 4:
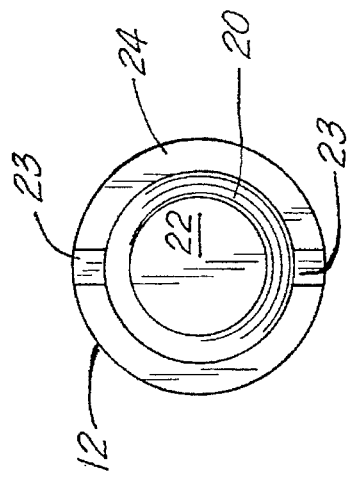
FIG. 4 is a fragmentary end view of the preferred embodiment of the apparatus of the present invention.

Central nail section 12 has opposing end portions 17, 18. A pair of frustroconically shaped projections 19, 20 are carried respectively by end portions 17, 18 as shown in FIG. 2. In FIGS. 3–5, central nail section 12 is shown including opposing frustroconical projecting connector portions 19, 20. The frustroconical projecting connector 19 includes a flat circular surface 21. The frustroconical connector 20 includes a flat circular surface 22. Each of the end portions 17, 18 provides keys 23 that are generally rectangularly shaped and positioned adjacent the frustroconical projections 19, 20 as shown in FIG. 3.

Keys 23 extend from annular shoulder 24 of each end portion 17, 18. Each frustroconical projection 19, 20 and it associated keys 23 and annular shoulder 24 cooperate with a similarly configured sockets 16, 25 respectively of proximal section 11 and distal section 13.

In FIG. 3, the distal section 13 and its socket 25 are illustrated. However, it should be understood that the end portion 15 of proximal nail section 11 carries a socket 16 that has a configuration and shape like that of the socket 25 shown in FIG. 3 for distal rod section 13. In this fashion, the proximal and distal nail sections 11, 13 affix at respective sockets 16, 25 to frustroconical projecting connectors 19, 20 on opposing respective ends 17, 18 of central section 12.

In FIG. 3, the socket 25 includes a frustroconical surface 26 that terminates at a flat circular surface 27 defining the inner most portion of the socket 25. Annular shoulder 28 cooperates with and abuts upon assemble of sections 12, 13, the annular shoulder 24.

Keys 23 are configured approximately 180° apart as are key slots 29 adjacent each socket 16, 29. Upon assembly, the frustroconical sections 19, 20 form a taper lock or morse taper connection with the respective socket 16, 25 of nail sections 11, 13. Upon assembly, the keys 23 align with and register into key slots 29 to provide an automatic indication of proper rotational alignment or a selected degree of anteversion. At the same time, the keys 23 and key slots 29 prevent rotation of one nail section relative to the adjoining nail section upon assembly.

Proximal nail section can have a pair of diagonally extending openings 30 that can receive bone screws for forming a connection between the nail 10 and adjoining bone. The proximal nail section 11 can have a central longitudinal bore 35 that intersects diagonal openings 30 at an angle of about 45°, for example. Transverse openings 31 are provides in distal rod section 13 for receiving bone screws therethrough. Similarly, the openings 31 can receive bone screws for affixing distal rod section 13 to adjoining bone tissue.

FIG. 1 illustrates modular intramedullary nail 10 as assembled. In FIG. 1, the assembled nail includes a proximal end 32 and a distal end 33. Circumferentially spaced slots 34 in proximal end 32 of proximal rod section 11 can accept insertion and/or removal tools for transmitting torque to the assembled nail 10 if desired. The central longitudinal bore 35 can include a threaded section for attaching a removal tool, bolt or the like to the proximal section 13 of the assembled nail 10 such as may be required during insertion or removal. Alignment arrows 36 can be used to aid the user in aligning keys 23 and key slots 29. The arrows 36 align as shown in FIG. 1. When keys 23 and key slots 29 are properly aligned and engaged.

The following table lists the parts numbers and parts descriptions as used herein and in the drawings attached hereto.

| PARTS LIST | |
|---|---|
| Part Number | Description |
| 10 | modular intramedullary nail |
| 11 | proximal section |
| 12 | central section |
| 13 | distal section |
| 14 | end |
| 15 | end |
| 16 | socket |

-continued

| PARTS LIST | |
|---|---|
| Part Number | Description |
| 17 | end |
| 18 | end |
| 19 | frustroconical projection |
| 20 | frustroconical projection |
| 21 | flat circular surface |
| 22 | flat circular surface |
| 23 | key |
| 24 | annular shoulder |
| 25 | socket |
| 26 | frustroconical surface |
| 27 | flat circular surface |
| 28 | annular shoulder |
| 29 | key slot |
| 30 | diagonal opening |
| 31 | transverse opening |
| 32 | proximal end |
| 33 | distal end |
| 34 | circumferentially spaced slots |
| 35 | bore |
| 36 | arrows |

The foregoing description should be considered exemplary of the invention and not restrictive. It should also be understood that improvements and modifications can be made to the invention without departing from the spirit and scope of the invention as defined in the appended claims.

We claim:

1. An implantable modular intramedullary nail, comprising:
    a) a proximal nail component
    b) a distal nail component;
    c) a central nail component having proximal and distal end portions that are respectively connected during use to the proximal and distal nail components to define therewith upon assembly a modular intramedullary nail unit of generally uniform outer diameter having a generally smooth continuous outer surface and that is free of sharp curves, enabling the assembled nail unit to be surgically inserted into a patient's intramedullary canal;
    d) connecting members for securing the proximal and distal nail components to the respective proximal and distal end portions of the central nail component, the connection members including corresponding conical socket and conical projecting end portions of adjoining nail components that can be fitted together and secured upon impact;
    e) self orienting interlocking portions positioned adjacent the respective conical socket and conical projecting end portions for resisting relative rotational movement between the components; and
    f) wherein the central nail component is much larger than either of the proximal or distal nail sections.

2. The modular nail of claim 1, wherein the self orienting interlocking members includes corresponding keys and key slots on the adjacent and connecting conical socket and conical projecting portions.

3. The modular nail of claim 1, wherein the proximal nail component has a partially internally threaded bore section.

4. The modular nail of claim 1, wherein the conical socket and conical projecting end portions are generally frustroconical in shape.

5. The modular nail of claim 1, wherein the central nail component has an annular shoulder at one end portion thereof.

6. The modular nail of claim 1, wherein the self orienting interlocking members include at least one cooperating key and a cooperating key slot.

7. The modular nail of claim 6, wherein said at least one key is formed adjacent one of the conical projecting end portions.

8. The modular nail of claim 1, wherein the proximal nail component has at least one transverse opening therethrough.

9. The modular nail of claim 1, wherein the distal nail component has at least one transverse opening therethrough.

10. The modular nail claim 4, wherein the self orienting interlocking members include a shaped projection on the male connector section, a corresponding shaped recess on the female connector section, and the projection and recess are shaped to engage for preventing relative rotational movement therebetween.

11. The modular nail of claim 1, wherein the central nail component is frustroconically shaped at each of its end portions.

* * * * *